United States Patent [19]

Teng et al.

[11] 4,239,664

[45] Dec. 16, 1980

[54] ANTI-THROMBOGENIC PVP-HEPARIN POLYMER

[75] Inventors: Lin-Nar Teng; Gottfried Schmer, both of Seattle, Wash.

[73] Assignee: Research Corporation, New York, N.Y.

[21] Appl. No.: 956,049

[22] Filed: Oct. 31, 1978

Related U.S. Application Data

[63] Continuation-in-part of Ser. No. 778,974, Mar. 18, 1977, abandoned.

[51] Int. Cl.$^3$ ............................................... C08L 5/10
[52] U.S. Cl. .................................. 260/17.4 R; 260/9; 424/9; 424/80; 424/183
[58] Field of Search ............... 260/9, 17.4 R; 424/183

[56] References Cited

U.S. PATENT DOCUMENTS

| | | | |
|---|---|---|---|
| 3,453,194 | 7/1969 | Bennett et al. | 204/159.12 |
| 3,457,098 | 7/1969 | Leininger et al. | 428/413 |
| 3,673,612 | 7/1972 | Merrill et al. | 260/9 |
| 3,846,353 | 11/1974 | Grotta | 260/9 |
| 4,087,567 | 5/1978 | Sullivan | 424/80 |

FOREIGN PATENT DOCUMENTS 680788  10/1952  United Kingdom ....................... 424/80

OTHER PUBLICATIONS

PVP, Lesser, Drugs and Cosmetic Industry, Jul. 1954: 75,1–pp. 32–37.

*Primary Examiner*—Edward M. Woodberry
*Attorney, Agent, or Firm*—John S. Roberts, Jr.

[57] ABSTRACT

The present invention relates to a group of novel compounds defined as covalently bound poly-N-vinyl pyrrolidinone (PVP)-heparins. These compounds are synthesized on the basis of a novel concept that heparin molecules can be modified to have new desirable qualities by binding heparin covalently to an appropriate polymer carrier which has the desired characteristics.

Heparin is hydrophilic and thereby insoluble in organic solvent. It has a short half-life in vivo. PVP-heparins, on the other hand, not only retain the anticoagulant activities of heparin, but also have the solubility (in organic solvents) and longer half-life in vivo of PVP.

PVP-heparins are produced either in anhydrous or heterogeneous media wherein PVP is activated by thionyl chloride to produce an imidoyl ion which is subsequently bound to heparin. PVP-heparin produced in anhydrous media is chloroform soluble and has been found useful for coating plastics and similar substances. PVP-heparin produced in heterogeneous media has been found to have twice the half-life in sheep as the native, unmodified heparin.

1 Claim, 9 Drawing Figures

Figure 1A:
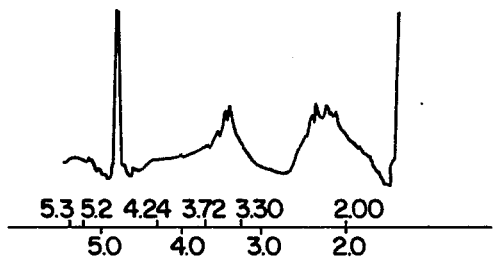
Figure 1B:
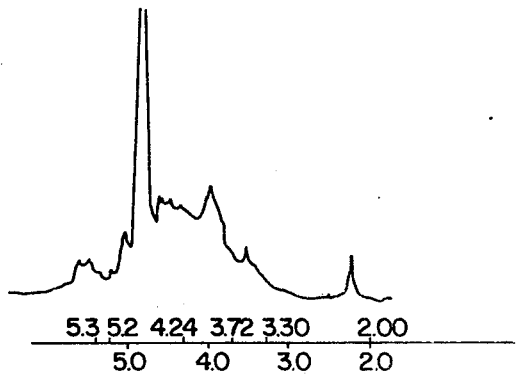
Figure 1C:
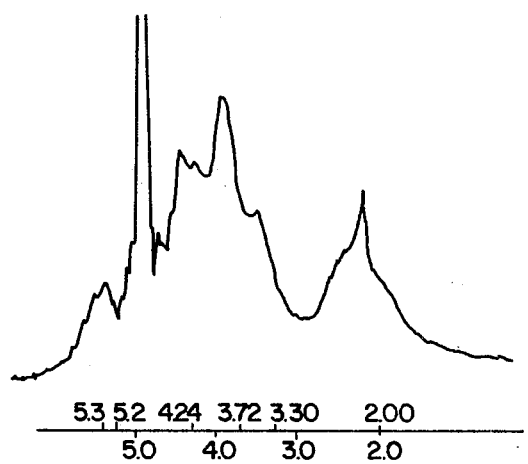
Figure 1D:
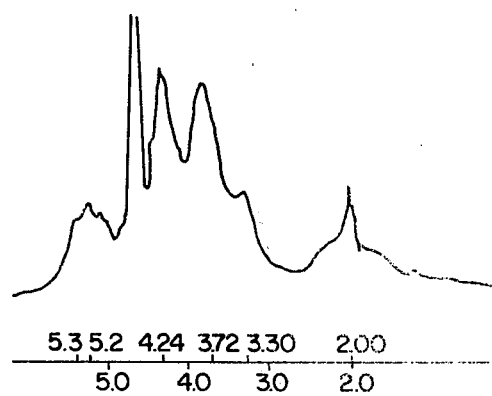

100 MHz PMR SPECTRUM OF:
FIG. 1A - PVP IN $D_2O$.
FIG. 1B - SIGMA HEPARIN IN $D_2O$.
FIG. 1C - PVP-HEPARIN H-II IN $D_2O$.
FIG. 1D - PVP-HEPARIN A-II IN $D_2O$.
CHEMICAL SHIFTS (P.P.M.) ARE RELATED TO TETRAMETHYL SILANE.

Figure 2A:
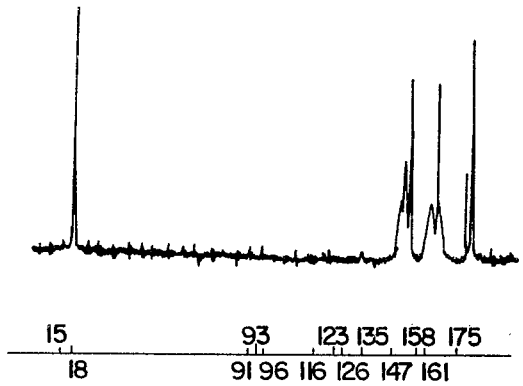
Figure 2B:
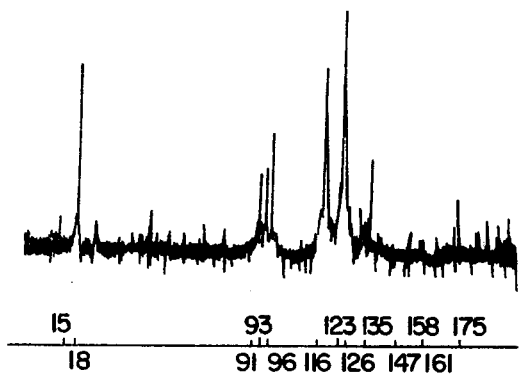
Figure 2C:
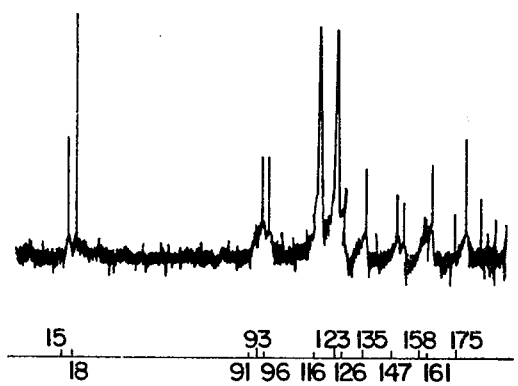
Figure 2D:
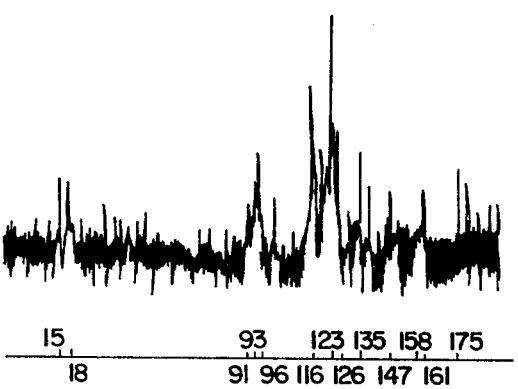

$^{13}$C FOURIER TRANSFORM NMR SPECTRUM OF:
FIG. 2A - PVP IN D$_2$O WITH PROTON DECOUPLING.
FIG. 2B - SIGMA HEPARIN IN D$_2$O WITH PROTON DECOUPLING.
FIG. 2C - PVP-HEPARIN H-II IN D$_2$O WITH PROTON DECOUPLING.
FIG. 2D - PVP-HEPARIN A-II IN D$_2$O WITH PROTON DECOUPLING.
CHEMICAL SHIFTS (P.P.M.) ARE RELATED TO DOWNFIELD CARBON DISULFIDE.

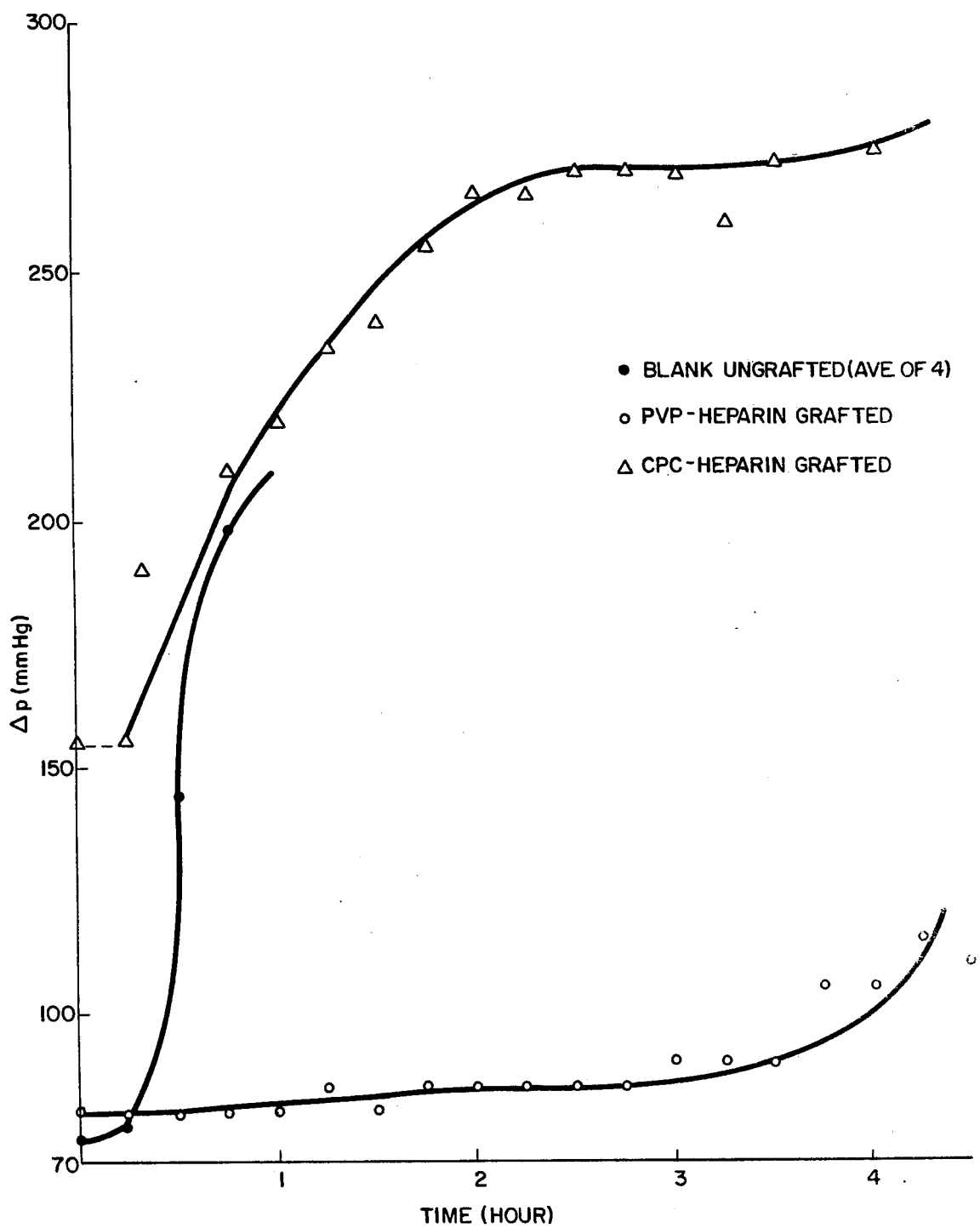

ANTI-THROMBOGENIC PVP-HEPARIN POLYMER

The invention described herein was made in the course of work under a grant or award from the Department of Health, Education, and Welfare.

The present application is a continuation-in-part of application Ser. No. 778,974, filed Mar. 18, 1977 and now abandoned.

The present invention relates to a group of novel compounds having non- or anti-thrombogenic qualities defined as covalently bound poly-N-vinyl pyrrolidinone (PVP)-heparins. These compounds are produced in either anhydrous or heterogeneous media wherein the PVP is activated by thionyl chloride to produce an imidoyl ion which is subsequently bound to heparin. The PVP-heparin compound which is prepared from anhydrous media is chloroform soluble and has been found useful for coating plastics such as silicone rubber, halocarbon plastics such as polyvinyl chloride, and similar substrates. The non-thrombogenic materials can be used for implanted and extracorporeal biomedical devices and prosthesis intended to be used in direct contact with blood, including tubes, valves, membrane assemblies for blood dialysis and oxygenation, anesthesia-carrying tubes, etc. The PVP-heparin compound which is prepared in heterogeneous media is found to have twice the half-life in sheep as does the native heparin. The advantages over prior heparin compounds are as follows: As a potential intravenous injection (i.v.) drug, PVP-heparin can maintain a low anticoagulant profile but with long sustaining anticoagulant effect. As coatings of plastics, the present method of formation is much simpler and more apt than where heparin is bound to polymer surfaces by chemical modification; e.g., hydroxy methyl methacrylate combined with heparin. In that case, the chemical process is too time-consuming and may alter the physical properties of the polymer surfaces. Also, in a second case, heparin is ionically attached through the polymer surface by formation of a complex with a quaternary ammonium salt; e.g., tridecylmethyl ammonium (TDMA)-heparin. The difficulty with this second method is that the quaternary ammonium ion within the surface is subject to potential toxicity in many cases when it is exposed to the blood.

PRIOR ART STATEMENT

As coating of plastics, the present invention is deemed novel over the following prior art.

(1) A. S. Hoffman and G. Schmer, C.A., 80:149087t (1974). This abstract deals with grafting a mixture of hydroxyethyl methacrylate and N-vinyl pyrrolidinone onto silicone rubber via a radiation grafting technique. Subsequently the OH groups from hydroxyethyl methacrylate on the polymer surface are activated via cyanogen bromide activation and covalently bound to heparin after the activation step. There is no participation by N-vinyl pyrrolidinone to form PVP-heparin.

(2) H. Tanzawa and Y. Mori, C.A., 80:30696a (1974). In this abstract there is no PVP-heparin but rather an ionic complex of heparin-benzalkonium which is entrapped and dispersed in a polymer matrix where polymerization of N-poly-(methyl methacrylate) provides the polymer network.

(3) U.S. Pat. No. 3,844,989 Harumiya et al. This patent, and particularly Example 10, shows a copolymer of vinyl acetate and N-vinyl pyrrolidinone which is subsequently quaternized with benzyl chloride. Undesired quaternary ammonium is present in this example which later adds heparin via the phrase "and heparinizing."

As a potential i.v. drug, the present invention is by far the first successful attempt to synthesize a long life heparin.

Relative to a substrate, the following are especially of interest: U.S. Pat. No. 3,453,194, Bennett et al; U.S. Pat. No. 3,457,098, Leininger et al (Quaternary and heparin on substrate); and U.S. Pat. No. 3,846,353, Grotta (Suitable polymers for substrate for heparin, see Column 2, wherein the suitable polymers listed are polyethylene, propylene, polyurethanes, polycarbonates, polystyrenes, polytetrafluoroethylene, silicone rubber, polyesters, nylons, natural rubber, polyvinyl chloride and acrylics).

DISCLOSURE OF THE INVENTION

BEST MODE FOR CARRYING OUT THE INVENTION

Polyvinyl pyrrolidinone, also known as poly-N-vinyl pyrrolidinone is a homopolymer, the structure of which may be expressed as follows:

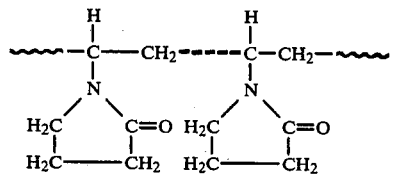

The homopolymer is water soluble and has long been used in pharmaceutical preparations.

Heparin is a mucopolysaccharide composed of sulfated D-glucosamine and D-glucuronic acid and has the following unit structure:

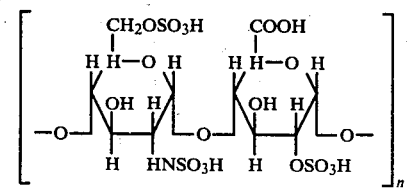

Anti-coagulant activity is related to sulfuric acid content and to molecular weight and size.

The novelty of the present invention lies in the formation of a compound PVP-heparin where the heparin is covalently bound to a biocompatible carrier polymer PVP which has solubility in organic solvents and which has a relatively long half-life in vivo. This binding between PVP and heparin seems not to affect the bioactivity of heparin as an anticoagulant. The PVP-heparin is non-toxic and has advantages over complexes of heparin-benzalkonium, heparin-tridecylmethyl ammonium (TDMA) and heparin-cetyl pyridinium. These latter heparinize polymer surfaces also operate through organic solvent permeation techniques but are potentially toxic when the heparinized surface is exposed to blood.

By the present preparation, a novel copolymer compound is obtained which may be expressed as PVP-heparin containing covalent linkages between the homopolymers and producing a copolymer compound which is antithrombogenic and which also has a long-lasting biological activity for heparin. The compound has been used successuflly in heparin-coated dialyzers and in coating the inner surfaces of plastic tubings for animal and clinical needs. Of great value is the property of PVP heparin in animal and clinical work since it is completely non-toxic.

The production of PVP-heparin in anhydrous medium (B) and in aqueous medium (C) is set out schematically below. It is noted that the process depends in both cases upon the activation of PVP producing the imidoyl ion of PVP which is set out as a preliminary step (A) for both processes.

(A) Activation of PVP

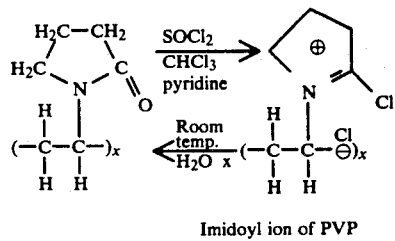

Imidoyl ion of PVP (B) Binding of Heparin to Imidoyl Ions of PVP in Anhydrous Medium

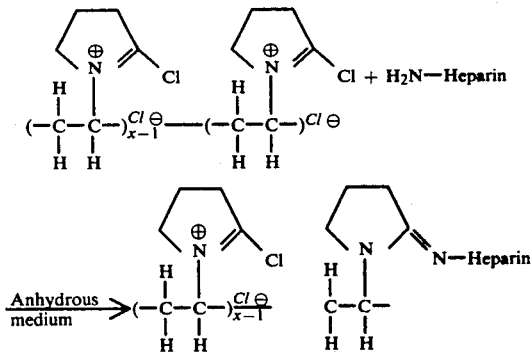

(C) Binding of Heparin to Imidoyl Ions of PVP in Aqueous Medium

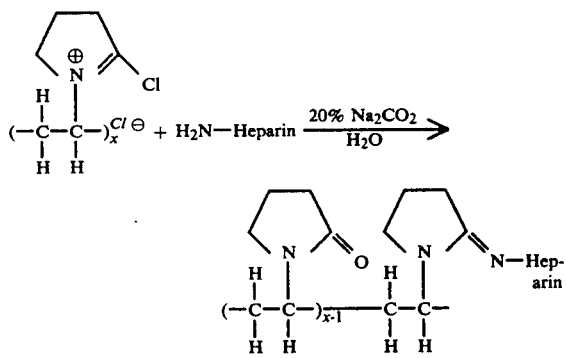

It has been shown that the carbonyl group of PVP with a molecular weight of 10,000 (a), 40,000 (b), and 360,000 (c), is activated by thionyl chloride to its imidoyl chloride which readily reacts with the amino groups of heparin to give a stable PVP-heparin compound where the heparin has a normal molecular weight of 6,000–20,000. The existence of this compound has been demonstrated by nuclear magnetic resonance, infra red spectra, hexosamine and uronic acid content and biological activity of a chloroform extract. Physicochemical data are shown in Table I below.

TABLE I

| | Solubility in Chloroform: Methanol + 2:1 (V/V) (g/100 ml) | Solubility in Water (g/100 ml) | % Biological Activity |
|---|---|---|---|
| Heparin | nil | 70 | 100 |
| PVP-Heparin | | | |
| a | 4.2 ± 0.2 | 14 | 26.8 |
| b | 3.2 ± 0.2 | 0.79 ± 0.10 | 11.7 |
| c | 2.9 ± 0.2 | 0.05 ± 0.10 | 1.3 |

Preliminary experiments with PVP-heparin (a) in sheep indicate an increase of the biological half-life time and on altered tissue distribution in the sense that most of the PVP-heparin remains in the blood compartment where its biological main function resides.

PVP-HEPARIN as an i.v. Injectable

In addition to its use as a coating of plastics, PVP-heparin is useful as an intravenous drug which has a long life in humans compared to normal heparin injection. The preparation (c) above is directed towards its later use as an intravenous injectable as shown in Example 3 as also set up in Table II under H-I and H-II.

EXAMPLE 1

Activation of Poly-N-Vinyl Pyrrolidinone (PVP, mol. wt. 10,000)—The Formation of Imidoyl Ion of PVP In a three-neck 500 ml round bottom flask equipped with a West condenser (air cooled) connected to a U-shaped Drierite drying tube, a pressure equilibrized dropping funnel and a glass stopper was stirred vigorously a solution of poly-N-vinyl pyrrolidinone (PVP) (6.0 g, 6×10$^{-4}$ mole or 0.054 unit weight of mono-N-vinyl pyrrolidinone) in 100 ml of chloroform and 20 ml of pyridine. Redistilled thionyl chloride (5 ml, 8.3 g, 0.119 mole) in 40 ml of chloroform was added dropwise to the above PVP solution.

The rate of addition was such that a gentle reflux of the reaction mixture was maintained. The addition lasted about ½ hour, and the solution changed from light yellow to clear dark reddish brown. The reaction solution was stirred and allowed to cool to room temperature for about 2 hours. The imidoyl ions of PVP were formed in chloroformpyridine solution.

EXAMPLE 2

Covalent Binding of Heparin to Poly-N-Vinyl Pyrrolidinone—Reaction in a Completely Anhydrous Media The reaction mixture from Example 1 was subjected to reduced pressure distillation to remove the excessive thionyl chloride as follows. The West condenser connected with the drying tube and dropping funnel were removed. In place of them were put in a Claisen distillation head with a fraction cutter and a glass stopper. Excessive thionyl chloride and some chloroform and pyridine (about 100 ml) were distilled off in vacuo at room temperature. Afterward, the distillation system was removed and the reflux system and a dropping funnel were re-installed. Through the dropping funnel, cetyl pyridinium chloride (CPC)-heparin complex (9.0 g in 300 ml of chloroform) was added at room temperature to the reaction mixture. The reaction mixture was subjected to heating below 68° C. (the b.p. of chloroform) for two hours. Subsequently, the mixture was stirred at room temperature overnight and a precipitate formed at the bottom of the reaction vessel.

This precipitate was slightly soluble in water and gave a positive test with 0.1% toluidine blue. The aqueous suspension of precipitate was extracted with chloroform (4×200 ml) in which it was soluble. The extracts were combined, evaporated in vacuo to dryness. The dry residue from the chloroform extracts was resuspended in distilled water, dialyzed against distilled water in a volume 100 times its original volume for 2 hours. The dialysate was lypholized to give 2.52 g of off-white powder, A-U, which was slightly soluble in water but soluble in $CHCl_3$. The toluidine blue test result here was non-definitive. The aqueous layer from the chloroform extraction step was dialyzed against distilled water 24 hours: 3×10 ml. Lypholization of the dialysate gave 1.96 g of cotton-like substance, A-II, soluble both in $CHCl_3$ and in water and gave a strong positive result from toluidine blue test. No appreciable heparin or heparin derivatives were recovered from the organic filtrate of the reaction mixture. Both A-I and A-II gave brownish complexes with chloroform-iodine solution indicating the presence of PVP.

EXAMPLE 3

Reaction of Heparin with Imidoyl Ions of PVP in Heterogeneous Medium

Heparin (8.49 g) in 75 ml of 20% $Na_2CO_3$ solution was added by stirring to imidoyl ions of PVP in chloroform-pyridine solution in which PVP (12.05 g, average mol. wt. 10,000, $1.2 \times 10^{-3}$ mole or 0.108 unit weight of mono N-vinyl pyrrolidinone) was activated by a slight excess of thionyl chloride (5.0 ml or 8.3 g, 0.119 mole). The addition lasted 30 minutes, during which heat and $CO_2$ evolved. The reaction mixture was stirred and allowed to cool down to room temperature.

Then the organic (chloroform-pyridine) layer of the solution mixture was separated from the aqueous layer. Evaporation of the organic layer under reduced pressure gave a residue with a trace of bitter odor (pyridine). The residue redissolved in a minimum of water. To the aqueous solution of the residue from the organic layer as well as to the aqueous layer from the reaction mixture, 50 ml of 5% cetyl pyridinium chloride (CPC) solution was added. White precipitates formed immediately. The precipitates were filtered. A small additional amount of 5% CPC solution was added to each of the filtrates to check the completion of CPC precipitation. Repetitive precipitations were needed for the filtrate obtained from the aqueous layer. PVP-heparin was recovered by dissolving the white CPC complex in 3.2 N $MgCl_2$, adding 50 ml of 2.5 N potassium thiocyanate to each of the solutions to precipitate CPC. Filtering the suspensions, the filtrate was dialzyed extensively against water as follows: 4 hours, 2×10 l; 24 hours, 2×10 l.

Lypholization of the dialysates gave white powders of 0.79 g from organic layer (H-I) and 6.35 g (H-II) from the aqueous layer, both gave positive toluidine blue tests and positive tests with chloroform-iodine solution. Repetitive precipitations from the filtrate obtained from the aqueous layer, after the usual operations mentioned above, gave H-II-A, 1.61 g, H-II-B, 2.06 g, and H-II-C, 0.16 g (cf Table II).

The bioactivity and solubility of PVP (mol. wt. 10,000)-heparins synthesized from heterogeneous media, i.e., H-I, H-II, H-II-A, H-II-B, H-II-C and those of PVP-heparins prepared in anhydrous media, i.e., A-I and A-II are shown in Table II. Because of low bioactivity in H-II-A, -B, -C, no further study on them has been done. It should be noted that H-I does retain some heparin bioactivity, even though its solvent solubility characteristics is entirely altered after the chemical modification.

After further purification by gel filtration in high salt using Sephadex G150 (15×900 mm) column, subsequently by desalting and lypholization PVP-heparins A-II and H-II with proven anticoagulant activity are subjected to analytical chemical analyses; i.e., elementary analysis, hexosamine content, uronic acid content, sulfate content, and PVP content. The results are shown in Table III.

TABLE II

Bioactivity and Solubility of PVP-Heparins

| Compound | Solubility (S) $CHCl_3$: MeOH = 2:1 (g/100 ml) | Solubility (S) $H_2O$ (g/100 ml) | Bioactivity Unit of Anticoagulant/mg |
|---|---|---|---|
| Sigma Heparin | Nil | >14.0 | 150 |
| PVP-Heparin | | | |
| A-I | 1.33* | Nil | — |
| A-II | 4.20 | >3.5 | 40.2 |
| H-I | 5.12 | 0.92 > S > 0.09 | 10 |
| H-II | 0.15 | >12.5 | 79.1 |
| -II-A | 6.0 | >14.0 | 0.5 |
| -II-B | 10.7 | >14.0 | 0.4 |
| -II-C | 12.3 | >10.5 | 4.2 |

*In $CHCl_3$ only

TABLE III

Chemical Compositions of Heparin and PVP-Heparins

| Compound | Elementary Analysis C %@ | H %@ | N %@ | S %@ | Na %* | Glucosamine % | Uronic Acid % | PVP % | $SO_4$ % |
|---|---|---|---|---|---|---|---|---|---|
| Sigma Heparin | 22.45 | 3.39 | 2.13 | 11.01 | 10.35 | 30.3 ± 2.5 | 41.6 ± 6.7 | | 31.7 ± 1.1 |
| PVP-Heparin A-II | 25.22 | 3.51 | 3.38 | 9.65 | 6.85 | 28.4 ± 3.4 | 39.4 ± 6.0 | 8.59 ± 0.59 | 29.7 ± 2.0 |
| PVP-Heparin H-II | 23.11 | 4.74 | 3.00 | 8.28 | 3.15 | 25.2 ± 4.0 | 33.8 ± 4.6 | 14.44 ± 0.79 | |

@Done by Chemalytics, Inc., Tempe Arizona.
*Done by Flame Atomic Emission Spectrametry.

EXAMPLE 4

Structure Elucidation of PVP-heparins by Proton $^1H$ and $^{13}C$ (Natural Abundance) Nuclear Magnetic Resonance (NMR) Spectroscopy Structure elucidations of PVP-Heparins A-II and H-II as well as the starting materials PVP (mol. wt. 10,000) and Sigma heparin have been performed using $^1H$ and $^{13}C$ (natural abundance) NMR spectroscopy.

The $^1H$, $^{13}C$ NMR has been obtained with a Varian CFT-20 ($^{13}C$, $^1H$ and $^1P$) or a Varian HA-100 ($^1H$) spectrometer using $D_2O$ as the source of lock signal. Samples were given a preliminary deuterium oxide--exchange by dissolving the deuterium oxide, lyophilizing the solution, and subsequently repeating the process at least three times.

For $^{13}C$ (natural abundance) NMR of Sigma heparin, PVP, and PVP-heparin H-II, 30% (by w/v) solution in deuterium oxide was used (0.90 g was used due to insufficient material (0.2 g in 3 ml $D_2O$). Sample solutions were each contained in a 12 mm tube, the spectrum width was 4,000 Hz, acquisition time about 1 sec, and pulse width 7 u sec. With concomitant proton decoupling, the total $^{13}C$ spectrum accumulation time varied from 18 hrs to 5 days in the case of PVP-heparin A-II.

The above solutions were also used to obtain proton magnetic resonance (PMR) spectra after a prior dilution of the above solutions with $D_2O$, deuteriate t-butanol was used as an internal standard. All spectra were done at room temperature.

The $^1H$ and $^{13}C$ NMR are shown in FIGS. 1 and 2, respectively. The PMR's and $^{13}C$ NMR's of PVP, Sigma heparin, PVP-heparins H-II and A-II shown in FIGS. 1 and 2 provides physical evidence of covalently bound PVP-heparin compounds.

In PMR of PVP (FIG. 1A), there is a broad multiplet around 2.0 p.p.m. indicating protons at C-3, C-5 and C-6, whereas the multiplet at downfield about 3.30 p.p.m. is found to be the signal of protons at C-2 and C-4. In the PMR of heparin (FIG. 1B), there is a singlet at 2.0 p.p.m., a signal of N-acetyl proton ($CH_3CO$-). The three signals locate further downfield of the strong DHO signal, i.e., 5.39, 5.20, 4.77 p.p.m. are assigned to be the protons at C-1 of the glucosamine unit (GH-1) and at C-1 and C-5 of the iduronic acid unit of heparin (i.e., IH-1 and IH-5). The multiplet between 4.41 to 4.71 p.p.m. are contributed by protons at carbons as follows: 4.41 p.p.m. (GH-5), 4.34 p.p.m. (IH-4), 4.25 p.p.m. (IH-2), 4.18 p.p.m. (IH-3), 4.07 p.p.m. (GH-2), 3.71 p.p.m. (GH-4 and GH-3), whereas GH-6 is overshadowed by DHO. Both the PMR of PVP-heparins (FIGS. 1C and 1D) have the combination of fine structures of heparin and PVP where two distinct features are most striking, (1) the heparin signals are found between 5.30 and 3.30 p.p.m., and (2) at 2.0 p.p.m. the singlet (N-acetyl proton of heparin is located on top the broad multiplet of PVP.

The $^{13}C$ NMR with proton decoupling spectra shown in FIGS. 2A, 2B, 2C and 2D also reaffirm what is observed in PMR spectra shown in FIG. 1. In FIG. 2A, signal at 15 p.p.m. is contributed by the carbonyl carbon of the lactam ring of PVP, the treplet at 146–148 p.p.m. are signals of C-2 and C-4, the ring carbons next to the lactam group. The multiplet at 158 p.p.m. is contributed by C-5 (150 p.p.m.), the carbon bound to N in the lactam ring, and by C-3 at about 161 p.p.m. The signal at 174.7 p.p.m. is contributed by C-6. In FIG. 2B, the signal carbonyl carbon of iuronic acid (I-6) is at 18 p.p.m. The signals at 93 and 96 p.p.m. are of I-1 and G-1. The two strong peaks 116 p.p.m. and 126 p.p.m. are signals of many carbons; 116 p.p.m. is that of I-2, I-4, G-4 and 126 p.p.m. is that of I-3, I-5, G-3 and G-5. The signal of G-6 is a shoulder peak next to 126 p.p.m. peak. G-2 signal is located at 135 p.p.m. The signals of PVP-heparins A-II and H-II are signals of the above two spectra combined. In FIG. 2C, not so apparent in FIG. 2D, the two carbonyl carbon signals locate at 15 and 18 p.p.m., the fine structures of heparin in the range of 91 to 135 p.p.m. and then the carbon signals in PVP appear from 147 to 175 p.p.m.

EXAMPLE 5

Pharmacokinetic Characterization of PVP (mol. wt. 10,000)-Heparin

Pharmacokinetic characterization of PVP-heparin molecules has been performed on their effectiveness as anticoagulants using healthy female sheep with carotid-jugular silastic cannulae (Quinton et al, Trans. Amer. Soc. Artic. Int. Organs, 8:236 (1962)). Commercial Sigma heparin and panheparin (Abbott Laboratory) were also determined pharmacokinetically as controls.

Procedure for Pharmacokinetic Characterization of PVP-Heparin

A single dose of PVP (mol. wt. 10,000)-heparin as well as commercially available Sigma heparin and panheparin (about 70 unit/kg body wt. in sterile saline) was injected into three fasting female sheep through the jugular cannula. Each sheep weighed approximately 70 kg. Blood samples were drawn from the carotid cannula prior to (0 time) and at various intervals (5 min, 10 min, 20 min, 30 min, 45 min, 1 hr, 1½ hr, 2 hr, 2½ hr, 3 hr, 4 hr, etc.) after injection. Blood is collected in 3% Na-citrate (9 parts blood to 1 part anticoagulant). All samples were processed were processed immediately after they were drawn. Blood samples were then centrifuged at 3,000 g (International for 10 min at room temperature. After separation of red cells, the platelet rich plasma was centrifuged at 22,000 g (Sorvall/RC2) at 4° C. for 30 min to give almost platelet-free plasma. All plasma was stored at $-80°$ C. until assay.

Pharmacokinetic Analysis of Data

The two compartment open model (Gibaldi, M., J. Pharm. Sci., 58:327 (1969) and Greenblat, D. J. et al, New Eng. J. Med., 293:702, 964 (1975)) was used to account for the pharmacokinetic behaviors of heparin and modified heparin in our studies. In this model, the body is assumed to be divided into two compartments with respect to the unchanged drug. The central compartment of small apparent volume consists of serum or blood together with extra-cellular fluid of highly perfused tissues such as heart, lungs, liver, kidneys, etc. The peripheral compartment of larger volume is formed by less perfused tissue such as skin, muscle, and body fat. The model assumes that drugs enter only via the central compartment and are eliminated only from the central compartment. Reversible transfer occurs between central and peripheral spaces so that the peripheral compartment acts as a "reservoir" connected only to the central compartment.

Three pharmacokinetic parameters are used to characterize the drug. They are half-life $T_{1/2}$, total apparent volume of distribution $V_D$, and clearance. One other important parameter is the apparent volume of the body fluid in which the unchanged drug is dissolved in the central compartment $V_1$. These four parameters will provide us with the half-life of the drug, its overall rate of elimination reaction, and its distribution in vivo.

Determination of the Effectiveness of Modified Heparin as an Anticoagulant

Heparin levels of the postheparin plasma were determined by the factor Xa inhibitor assay (Yin et al, J. Lab.

Clin. Med., 81:298 (1973)) and by the partial thromboplastic time. Fresh whole blood recalcification time will also be done.

The pharmacokinetic profiles of panheparin (ave. of 5 runs), Sigma heparin (ave. of 4 runs), PVP (mol. wt. 10,000)-heparin A-II (ave. of 2 runs), and PVP (mol. wt. 10,000)-heparin H-II (ave. of 5 runs) are shown in Table IV. The doses, half-life $T_{1/2}$, the apparent volume of the body fluid in which the unchanged drug is dissolved in the central compartment $V_1$, the total apparent volume of distribution $V_D$, and clearances of each heparin are also tabulated in Table IV.

Seventy kilograms (the body weight of each sheep used in this pharmacokinetic study) is just about the average weight of a man. The half-life of heparin in man (healthy volunteer) is 1 - 1½ hour in whatever way it is measured. This half-life (1 - 1½ hr in man) does not increase with doses from 65 unit/kg to 130 unit/kg (Estes, Ann. N.Y. Acad. Sci., 179:191 (1971)). This is approximately the range of doses of native heparins or PVP-heparins used in this study.

The results are summarized as follows.

1. The pharmacokinetic profiles of heparins show that the logarithm of plasma heparin (anticoagulant) concentration versus time after injection of heparins or PVP-heparins, except PVP-heparin H-II, follows first order kinetics. In the case of PVP-heparin H-II, there are bifacial curves with two distinct linear components, the distribution phase and the elimination phase. Each phase follows first order kinetics. The distribution phase is not observed in cases of panheparin, Sigma heparin, and PVP-heparin A-II.

2. The heparin (or PVP-heparin) dose range used in this pharmacokinetic study is 6–120 unit/kg, where the half-life in man is found to be unchanged. In this dose range, the half-lives of commercial heparins in sheep are $1.04 \pm 0.30$ hour for panheparin, and $1.00 \pm 0.09$ hour for Sigma heparin. They are literally identical. The half-life of PVP-heparin A-II in sheep is $0.70 \pm 0.07$ hour and that of PVP-heparin H-II in sheep is $2.09 \pm 0.51$ hours. The half-life of PVP-heparin H-II in sheep is twice as long as those of native Sigma heparin and panheparin in sheep (see Table IV).

3. In one single case where the dose of PVP-heparin A-II used is 302 unit/kg, the half-life of heparin in sheep is lengthened to 1.7 hr, as compared with $0.70 \pm 0.07$ hr of the same heparin derivatives. This has also been observed in man when the range of doses is wide, i.e., dose given in mg/kg and varied from 1 mg/kg to 10 mg/kg (Estes, J. W., Ann. N.Y. Acad. Sci., 179:191 (1971)). It should be noted that half-life of high dose PVP-heparin A-II (302 unit/kg=2 mg/kg of native heparin), though prolonged (1.7 hr), does not exceed that of PVP-heparin H-II ($2.09 \pm 0.51$ hrs) in spite of the fact that the dose of the latter is only one-third of the former.

4. Native heparins, i.e., panheparin, Sigma heparin, and PVP-heparin A-II, have identical $V_D$, the total apparent volume of distribution, and $V_1$, the apparent volume of the body fluid in which the unchanged drug is dissolved in the central compartment. This suggests that the i.v. drugs distribute mostly in the central compartment and almost nil in the peripheral compartment. On the other hand, $V_D$ of PVP-heparin H-II ($4,145 \pm 785$ ml) is twice that of $V_1$ ($2,069 \pm 341$ ml), indicating that half of the amount of the injected drug is in the peripheral compartment. Since the $V_D$ of PVP-heparin H-II is in the same range (3,000–5,000 ml) of the $V_D$ of Sigma heparin, panheparin, and PVP-heparin A-II, its reduction in $V_1$ is a showing that binding PVP covalently to heparin molecule in heterogeneous media results in a compound which alters the pharmacokinetic distribution in vivo (see Table IV).

5. The clearance of PVP-heparin H-II ($23.55 \pm 4.19$ ml/min) is much smaller than those of panheparin ($38.37 \pm 5.79$ ml/min), Sigma heparin ($56.00 \pm 10.45$ ml/min), and PVP-heparin A-II ($76.07 \pm 2.37$ ml/min). This also shows that molecular modification of heparin does alter the overall rates of elimination and metabolic reaction of PVP-heparin H-II in vivo. cl EXAMPLE 6

Test for Effectiveness of Polymer Heparinization; Duration of Anti-Coagulant Activity in a "Pseudo" Hemodialysis Unit As noted ante, PVP-heparin is soluble in organic solvents and can thereby be utilized to grant certain polymers using organic solvent permeating techniques (Schmer et al, Trans. Amer. Soc. Artif. Organs, 22:654 (1976)). In this laboratory, much of the effectiveness of polymer grafting technology has been done in vivo using hollow fiber artificial kidney (HFAK) with 22 ft of PVC (polyvinyl chloride) blood tubing set on sheep. With this method, the HFAK seems to function according to the anti-coagulation of the grafted polymer systems (Schmer et al, Proc. Dialysis Transplant Forum, 46 (1973); Schmer et al, Kidney Int., 7:5431 (1975); and Schmer et al, Trans. Amer. Soc. Artif. Organs, 22:654 (1976)) (A Totally heparinized system of the same device has been successfully used for hemodialysis of renal patients, see Schmer et al, Trans. Amer. Soc. Artif. Organs, 23:177 (1977)).

Three percent of PVP (mol. wt. 360,000)-heparin compound in chloroform:methanol=2:1 (by V/V) and 3% cetyl pyridinum chloride (CPC)-heparin complex in chloroform solutions were drawn into the respective blood tubing sets by suction and allowed to diffuse into the plastic for 5 mins. The tubing was then sucked through these grafted sets by an aspirator for 30 mins to achieve uniform drying of the coating. Further drying was accomplished by an air stream filter through a KOH-Drierite column over night.

In the test, the PVP-heparin or CPC-heparin grafted tubing set is connected to a modified but ungrafted HFAK Cordis-Dow Model VI. The HFAK is reduced to 1/6 of its original volume with a surface area reduced to about 1,000 cm$^2$. The two ends of the dialysis system are connected to the carotide, jugular cannulae of the sheep respectively, and the experiment begins. The anticoagulation of the system is solely maintained by the release of PVP-heparin which has been grafted to the blood tubing set. The performance of the system is gauged by performing the above-described experiment with PVP-heparin grafted system and at separate times, control experiments with the same system which has not been grafted. Relative performance is assessed in grafted and control system by comparison of (1) progressive clot formation in the HFAK, (2) the rate of fiber bundle volume loss (FBVL) in percentage per hours, (3) the time of the experiments until system clotting, as indicated by pressure change, reaches predetermined termination levels, and (4) changes observed through hematological and coagulation monitoring before, during, and after the dialysis run.

For assessment of PVP-heparin as coating of plastics, a system of ungrafted blood tubing sets is used as a low control and a system of CPC-heparin as known in the prior art (see Schmer et al 1976, 1977) grafted tubing sets as high control. For the hematological and coagulation monitoring purpose, blood samples were taken at the venous end of the HFAK before the system is connected to the sheep, in the middle of the run, i.e., 2 hrs after the run began, and at the end of the run. The dialysis time is too short for the control system to have middle sample taken.

The results are shown in FIG. 3 and Tables V and VI.

1. The performance of PVP-heparin granted blood tubing sets in terms of the anticoagulation of the dialysis system is equal to or better than that of the sets grafted by CPC-heparin complex as indicated in their P profiles (see FIG. 3), their rate of fiber bundle volume loss (FBVL, in %/hr), and their time length of the experiment until the system clotted (see Table V).

2. Both PVP-heparin and CPC-heparin grafted systems have at least 4 times better performance than does the control system as indicated by the average dialysis time; control, 1.01±0.29 hr, PVP-heparin, 4.75 hrs, CPC-heparin, 4.0 hrs, and by ave. FBVL; control, 62.0±44.1 (%/hr), PVP-heparin, 16.9 %/hr and CPC-heparin, 17.7 %/hr.

3. There is anticoagulation activity (in terms of heparin activity) released from the blood tubing sets to the system as evidenced by the prolongation in thrombin times and partial thromboplastic times observed in the mid. samples taken from the runs of PVP-heparin and CPC-heparin grafted systems.

The amount of heparin activity released by PVP-heparin grafted tubing was determined by Yin and Wessler's Xa neutralization assay to be 0.5 unit/ml. min.

TABLE IV

Hematology and Coagulation of Dialysis Runs

| Test | System Sample | Control Start | Control End | PVP (mol. Wt. 360,000) Heparin Coated Blood Tubing Set | | | CPC . Heparin Coated Blood Tubing Set | | | Control Value |
|---|---|---|---|---|---|---|---|---|---|---|
| | | | | Start | Mid | End | Start | Mid | End | |
| HCT (%) | | 32.2 ± 2.6 | 27.0 ± 2.7 | 34 | 25 | 26 | 37 | 29 | 27 | |
| Platelet ($\times 10^3$) | | 571 ± 90 | 472 ± 97 | 524 | 454 | 420 | 634 | 502 | 444 | |
| Thrombin Time (sec) | | 15 ± 3 | 17 ± 2 | 13 | 200* | 13 | 15 | 200 | 21 | 17 ± 1 |
| Partial Thromboplastin Time | | 60 ± 14 | 60 ± 11 | 66 | 200* | 66 | 56 | 200 | 89 | 39 ± 3 |
| Fibrinogen (mg%) | | | | | | | | | | |
| Laury | | 163 ± 91 | 152 ± 83 | 124 | 110 | 108 | 95 | 87 | 93 | |
| Jacobsen | | 378 ± 263 | 353 ± 244 | 253 | 229 | 242 | | | | |

*The heparin leaching is about 0.5 unit/ml/min determined by Yin and Wessler's Xa neutralization assay.

TABLE V

Comparative Performance of Heparin Modification Grafted Systems Versus Ungrafted Systems

| Experimental System | Number Run | Ave. FBVL (%/hr) | Ave. Dialysis Time (hr) |
|---|---|---|---|
| Blank | 4 | 62.0 ± 44.1 | 1.01 ± 0.29 |
| PVP-Heparin Coated Blood Tubing Set | 1 | 16.9 | 4.75 |
| CPC . Heparin Coated Blood Tubing Set | 1 | 17.7 | 5.0 |

We claim:

1. An anti-thrombogenic chloroform soluble polymer compound where the PVP has a molecular weight of 10,000 to 360,000 and heparin has a normal molecular weight of 6,000 to 20,000 consisting essentially of a covalently bound poly-N-vinyl pyrrolidinone (PVP)-heparin formed by activating PVP with thionyl chloride to form an imidoyl ion and bonding heparin, said polymer compound being useful as a protracted i.v. therapeutic drug in humans.

* * * * *